United States Patent
Cervenka

(10) Patent No.: US 6,646,171 B2
(45) Date of Patent: Nov. 11, 2003

(54) PROCESS FOR THE CRYSTALLIZATION OF STERICALLY HINDERED COMPOUNDS

(75) Inventor: Jan Cervenka, Oslo (NO)

(73) Assignee: Amersham Health AS, Oslo (NO)

( * ) Notice: Subject to any disclaimer, the term of this patent is extended or adjusted under 35 U.S.C. 154(b) by 1 day.

(21) Appl. No.: 09/986,974

(22) Filed: Nov. 13, 2001

(65) Prior Publication Data

US 2002/0072639 A1 Jun. 13, 2002

Related U.S. Application Data

(63) Continuation of application No. 09/538,492, filed on Mar. 30, 2000, now abandoned, which is a continuation of application No. PCT/GB98/02955, filed on Oct. 2, 1998.
(60) Provisional application No. 60/069,925, filed on Dec. 17, 1997.

(30) Foreign Application Priority Data

Oct. 2, 1997 (GB) ............................................. 9720969

(51) Int. Cl.[7] ............................................. C07C 17/38
(52) U.S. Cl. ........................ 570/177; 570/178; 570/262
(58) Field of Search ................................. 570/177, 178, 570/262

(56) References Cited

U.S. PATENT DOCUMENTS 4,250,113 A    2/1981    Nordal

FOREIGN PATENT DOCUMENTS

| DE | 44 25 340 A | 12/1994 |
|----|-------------|---------|
| EP | 0 108 638 A | 5/1984  |
| EP | 0 747 344 A | 12/1996 |
| GB | 2 280 436 A | 2/1995  |

Primary Examiner—Johann Richter
Assistant Examiner—Elvis O. Price
(74) Attorney, Agent, or Firm—Robert F. Chisholm

(57) ABSTRACT

A process for the crystallisation of a sterically hindered organic compound from a saturated or supersaturated solution of said compound in a solvent therefor, characterised in that crystallisation is effected under elevated pressure at a temperature above the boiling point of said solution at atmospheric pressure and up to the boiling point of said solution at said elevated pressure.

8 Claims, No Drawings

PROCESS FOR THE CRYSTALLIZATION OF STERICALLY HINDERED COMPOUNDS

This application is a continuation of application Ser. No. 09/538,492, filed Mar. 30, 2000 (of which the entire disclosure of the pending, prior application is hereby incorporated by reference), now abandoned, which is a continuation of international application number PCT/GB98/02955, Oct. 2, 1998, which was published in English, which itself is a continuation-in-part of U.S. provisional application No. 60/069,925, filed Dec. 17, 1997.

This invention relates to a process for the crystallization from solution of a chemical species having multiple conformations with steric hindrance to transitions between such conformations.

The vast majority of organic compounds are capable of adopting different conformations, generally as a result of rotations about sigma bonds. Where the compounds contain bulky groups however there is significant steric hindrance to such rotations and as a result transitions between stable (or metastable) conformations occur relatively slowly.

For crystallization of a substance to occur, the substance must adopt the conformation required by the crystalline structure. Accordingly, crystallization of sterically hindered compounds can take place relatively slowly. A high degree of supersaturation is normally required for acceleration of crystallization, resulting in limited purity in the crystalline product.

This is the case for example with the iodophenyl compounds commonly used as X-ray contrast agents and is particularly true for the so-called dimeric compounds which contain two iodophenyl groups per molecule, e.g. compounds such as iodixanol and iotrolan, which may take days to crystalize.

As a result, the manufacture of such compounds is extremely demanding in terms of time and equipment.

We have now found that crystallization of such sterically hindered compounds from solution may be accelerated, and/or the need for a high degree of supersaturation may be reduced, by crystallization with high thermal energy. The necessary thermal energy can be achieved by use of a boiling solvent (or boiling solvent mixture) or crystallization under pressure.

Crystallization under pressure is performed at temperatures above the boiling point (at atmospheric pressure) of the solution.

The invention thus provides a time-saving method and/or a method which will improve the purity of the product.

Thus viewed from one aspect the invention provides a process for the crystallization of a sterically hindered organic compound from a saturated or more preferably supersaturated solution of said compound in a solvent therefor, characterised in that crystallization is effected with high thermal energy.

One preferred aspect of the invention provides a process for the crystallization of a sterically hindered organic compound from a saturated or more preferably supersaturated solution of said compound in a solvent therefor, characterised in that crystallization is effected under elevated pressure at a temperature above the boiling point of said solution at atmospheric pressure (ie. ambient pressure, e.g. 1 bar) and up to the boiling point of said solution at said elevated pressure.

The necessary thermal energy may also be achieved by crystallization at the boiling point of the solvent or solvent mixture at atmospheric conditions. Under such working conditions the thermal energy input is limited by the boiling point of the solvent or solvent mixture used.

Thus a further preferred aspect of the invention provides a process for the crystallization of a sterically hindered organic compound from a saturated or more preferably supersaturated solution of said compound in a solvent therefor, characterised in that crystallization is effected at the boiling point of the solvent or solvent mixture used.

In the processes of the invention, the supersaturated solution may for example be produced from a non-saturated solution (e.g. by evaporation of a solvent or by cooling), or by dissolving amorphous material at elevated temperatures, or by the addition of a material (e.g. an anti-solvent) which reduces the solubility in the solvent system of the substance to be crystallized.

Crystallization from the supersaturated solution may be started by the use of a crystallization initiator, e.g. seed crystals of the sterically hindered compound. These may be added to the supersaturated solution before, during or after temperature and pressure are raised.

The solvent used in the processes of the invention may be a single solvent or a solvent mixture. Any solvent or solvent mixture capable of forming a liquid solution of the sterically hindered compound may be used although solvents such as water, alcohols, ketones, esters, ethers, and hydrocarbons are preferred, especially water, alcohols, alcohol-ethers, ethers and ketones, e.g. $C_{1-4}$ alcohols.

Examples of suitable solvents include water, methanol, ethanol, n-propanol, isopropanol, n-butanol, i-butanol, sec-butanol, t-butanol, pentanols including isoamyl alcohol, methoxyethanol, ethylene glycol, propylene glycol, acetone, ethyl-methyl ketone, formaldehyde, acetaldehyde, dimethyl ether, diethylether, methylethyl-ether, tetrahydrofuran, ethylacetate, methyl cyanide, dimethylsulphoxide, dimethylformamide, benzene, toluene, xylene, n-hexane, cyclohexane, n-heptane, etc.

Especially preferably, the solvent comprises one or more $C_{1-6}$ alkanols, alkoxyalkanols, linear or cyclic ethers, optionally together with a minor quantity (e.g. up to 10 wt %) of water.

Especially preferably, the solvent or solvent mixture used is a low-boiling or moderate boiling point material, e.g. having a boiling point of −10 to +100° C. at ambient pressure, especially 30 to 80° C., particularly 40 to 70° C. The solvent or solvent mixture however should be stable at the temperature and pressure conditions used. It is also preferred that the crystallization be effected at a temperature below 200° C., especially below 150° C. and most preferably below 120° C., and for crystallization under pressure that this be a temperature at least 10° particularly at least 15° C. above the boiling point of the solution under ambient pressure.

An added advantage of the pressure crystallization aspect of the invention is that the solubility of the sterically hindered compound is higher at the temperatures used than at temperatures below the boiling point of the solution at ambient pressure. As a result, the quantity of solvent used can be reduced as can the volume of the crystallizer vessel. Moreover solvents in which the sterically hindered compound is only relatively poorly soluble under ambient conditions may be usable and as a result it may be feasible to use more environmentally friendly solvent systems for crystallization (or recrystallization).

The sterically hindered compound crystallized according to the processes of the invention will preferably be a compound having at ambient temperature in solution (e.g. in water, $C_{1-4}$ alcohol or $C_{1-4}$ ether) at least two stable conformations with an activation energy at ambient conditions of at least 50 kJ/mole, preferably at least 80 kJ/mole, and preferably no more than 200 kJ/mole, for transition between these conformations. This activation energy may be calculated by standard techniques of quantum chemistry, etc.

In general, the processes of the invention are suitable for compounds which have a high activation energy for crystal growth, e.g. higher than 50 kJ/mole.

Examples of suitable compounds include hydroxyalkyl and/or acylamino and/or alkylaminocarbonyl derivatives of 2,4,6-triiodophenyl monomers and dimers such as those proposed or used as X-ray contrast agents (and in particular the non-ionic agents), for example diatrizoate, iobenzamate, iocarmate, iocetamate, iodamide, iodipamide, iodixanol, iohexol, iopentol, ioversol, iopamidol, iotrolan, iodoxamate, ioglicate, ioglycamate, iomeprol, iopanoate, iophenylate, iopromide, iopronate, ioserate, iosimide, iotasul, iothalamate, iotroxate, ioxaglate, ioxitalamate, metrizamide and metrizoate, as well as the monomers and dimers of WO96/09285 and WO96/09282.

Besides such iodinated x-ray contrast agents, the processes of the invention are also applicable to crystallization of other sterically hindered compounds, in particular pharmaceutical compounds, especially substances having highly restricted side chain rotations or other conformational changes. Such substances should of course be crystallized at temperatures at which they are stable. The processes moreover are applicable to all substances with low solubility in a selected low-boiling solvent regardless of the activation energy of the steric changes.

The pressure applied in the pressure crystallization aspect of the invention will conveniently be such as to ensure that the boiling point of the saturated or supersaturated solution is raised relative to the boiling point at ambient pressure by at least 10° C., especially at least 15° C. and more especially at least 20° C. The maximum pressure will generally be dictated by design constraints on the apparatus used but in general an overpressure of 0.05 to 20 bar, particularly 0.2 to 10 bar, especially 1.5 to 6 bar may be used.

The crystallization should therefore be performed in a vessel capable of withstanding the temperature and pressure conditions used. In general a stainless steel batch or continuous reactor equipped for stirring, heating and provided with means for applying and releasing pressure may be used.

In the "boiling point" aspect of the invention the choice of solvent will reflect not only the capability to form a liquid mixture, but also the need for thermal energy in order to achieve an effective crystallization process. The process is especially suitable for the crystallization of iodixanol with the solvent being methanol or a mixture of methanol (0–100% by volume), propan-2-ol (0–80% by volume) and water (0–10% by volume).

The invention will now be described with reference to the following non-limiting Examples:

EXAMPLE 1

80 g of solid iodixanol containing 3% wt water was dissolved in 374 mL methanol under reflux under ambient pressure. 48 mL of propan-2-ol were added and the solution was seeded with 1.6 g of iodixanol crystals. The mixture was maintained under reflux and the crystallization was followed by monitoring the iodixanol content of the mother liquor. When this had stabilized after 24 hours, the crystalline iodixanol was removed.

Yield: 89% (24 hours)

EXAMPLE 2

An iodixanol solution prepared and seeded as in Example 1 was placed in an autoclave and stirred for 5 hours at 90° C. under an overpressure of about 2 bar. The autoclave was cooled and the crystalline iodixanol recovered.

Yield: 91%

EXAMPLE 3

150 g of dry raw iohexol has been dissolved in 50 ml 2-methoxyethanol in an autoclave. 1.5 g iohexol seeds were added and the solution heated up to 100° C. A solubility gradient was created by a controlled addition of 150 ml 2-propanol (b.p. 82.4° C.) during a 5-hour period at constant temperature 100° C., followed by a controlled cooling to 70° in 3 hours. After additional 3 hours equilibration, the crystals were filtered off and washed by 2-methoxyethanol/2-propanol and finally dried.

Yield: 90%

Purity: 99.1%

A reference experiment ran under reflux provided a purity of 98.6%.

What is claimed is:

1. In a process for the crystallization of a sterically hindered organic compound form a saturated or supersaturated solution of said compound in a solvent therefor, the improvement comprising crystallizing said compound under elevated pressure at a temperature at least 10° C. above the boiling point of said solution at atmospheric pressure (1 bar) and up to the boiling point of said solution at said elevated pressure.

2. The process of claim 1 wherein said sterically hindered compound is a triiodophenyl group containing compound.

3. The process of claim 1 wherein said solvent has a boiling point at atmospheric pressure (1 bar) of −10 to +100° C.

4. The process of claim 1 wherein said elevated pressure is an overpressure of from 0.005 to 20 bar.

5. The process of claim 1 wherein the solvent comprises one or more $C_{1-6}$ alkanols, alkoxyalkanols or linear or cyclic ethers.

6. The process of claim 5 wherein the solvent further comprises up to 10% by weight of water.

7. The process of claim 1 wherein said compound is iodixanol or iohexol.

8. The process of claim 1 wherein said compound is iodixanol and said solvent is methanol or a mixture of 0–100% by volume methanol, 0–80% by volume propan-2-ol and 0–10% of volume by water.

* * * * *